United States Patent
Zhu et al.

(10) Patent No.: US 10,593,234 B2
(45) Date of Patent: Mar. 17, 2020

(54) CARDIAC VIRTUALIZATION TEST TANK AND TESTING SYSTEM AND METHOD

(71) Applicant: Acutus Medical, Inc., Carlsbad, CA (US)

(72) Inventors: Min Zhu, San Diego, CA (US); Derrick R. Chou, San Diego, CA (US); Graydon E. Beatty, Bloomington, MN (US); R. Maxwell Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 51 days.

(21) Appl. No.: 15/569,231

(22) PCT Filed: May 11, 2016

(86) PCT No.: PCT/US2016/031823
§ 371 (c)(1),
(2) Date: Oct. 25, 2017

(87) PCT Pub. No.: WO2016/183179
PCT Pub. Date: Nov. 17, 2016

(65) Prior Publication Data
US 2018/0315347 A1   Nov. 1, 2018

Related U.S. Application Data

(60) Provisional application No. 62/160,501, filed on May 12, 2015.

(51) Int. Cl.
*G09B 23/32* (2006.01)
*G09B 23/28* (2006.01)
(Continued)

(52) U.S. Cl.
CPC .......... *G09B 23/32* (2013.01); *A61B 5/04021* (2013.01); *G09B 23/288* (2013.01);
(Continued)

(58) Field of Classification Search
CPC ................. A61B 5/0422; A61B 2505/09; G09B 23/288; G09B 23/303; G09B 23/32
See application file for complete search history.

(56) References Cited

U.S. PATENT DOCUMENTS 4,173,228 A    11/1979   Van Steenwyk et al.
5,041,973 A  *  8/1991   Lebron .............. A61B 5/04021
                                                         703/11
(Continued)

FOREIGN PATENT DOCUMENTS

CA         2829626       9/2012
CN        201223445      4/2009
(Continued)

OTHER PUBLICATIONS

Anatomy Warehouse, "Axis Heart Model", 2014, pp. 1-3, at http://www.anatomywarehouse.com/axis-scientific-2-part-deluxe-life-size-human-heart-a-104269. (Year: 2014).*
(Continued)

*Primary Examiner* — Steve Rowland
(74) *Attorney, Agent, or Firm* — Onello & Mello, LLP (57) ABSTRACT

Provided is a cardiac virtualization test tank and testing system and method. A test tank is provided that includes a physical heart model representing the structure of the heart and a plurality of electrodes that output simulated biopotential signals based on an EP model representing the electrophysiological activity of the heart. The test system can be used for training, teaching, or validating a cardiac mapping, diagnosis, and/or treatment system, as examples.

21 Claims, 5 Drawing Sheets

(51) Int. Cl.
  *G09B 23/30*   (2006.01)
  *A61B 5/0402*  (2006.01)
  *A61B 5/042*   (2006.01)

(52) U.S. Cl.
  CPC .......... *G09B 23/303* (2013.01); *A61B 5/0422* (2013.01); *A61B 2505/09* (2013.01)

(56) References Cited

U.S. PATENT DOCUMENTS

| | | |
|---|---|---|
| 5,156,151 A | 10/1992 | Imran |
| 5,293,868 A | 3/1994 | Nardella |
| 5,482,472 A * | 1/1996 | Garoni .................. G09B 23/30 345/83 |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesely et al. |
| 5,795,299 A | 8/1998 | Eaton et al. |
| 5,820,568 A | 10/1998 | Parker |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 * | 2/2001 | Noren .................. A61N 1/3712 607/28 |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,574,492 B1 | 6/2003 | Ben-Haim et al. |
| 6,640,119 B1 | 10/2003 | Budd et al. |
| 6,716,166 B2 | 4/2004 | Govari |
| 6,728,562 B1 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,505,810 B2 | 3/2009 | Harlev et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,208,998 B2 | 6/2012 | Beatty et al. |
| 8,233,972 B2 | 7/2012 | Zhang |
| 8,311,613 B2 | 11/2012 | Danehorn |
| 8,320,711 B2 | 11/2012 | Altmann et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,757,044 B2 | 9/2017 | Scharf et al. |
| 9,827,039 B2 | 11/2017 | Dandler et al. |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,082,395 B2 | 9/2018 | Koyrakh et al. |
| 2001/0007070 A1 | 7/2001 | Stewart et al. |
| 2002/0026118 A1 | 2/2002 | Govari |
| 2002/0128565 A1 | 9/2002 | Rudy |
| 2002/0165441 A1 | 11/2002 | Coleman et al. |
| 2003/0036696 A1 | 2/2003 | Willis et al. |

(56) References Cited

U.S. PATENT DOCUMENTS

| | | |
|---|---|---|
| 2003/0065271 A1 | 4/2003 | Khoury |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0279263 A1* | 11/2010 | Duryea ............ G09B 23/28 434/267 |
| 2010/0286551 A1 | 11/2010 | Harlev et al. |
| 2010/0298690 A1 | 11/2010 | Scharf |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1* | 4/2012 | Schwartz ............ G09B 23/285 434/262 |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1* | 12/2013 | Rubinstein ............ G09B 23/285 434/272 |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2017/0035486 A1 | 2/2017 | Lopes et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 1/2018 | Scharf et al. |
| 2018/0146948 A1 | 5/2018 | Chou et al. |

FOREIGN PATENT DOCUMENTS

| | | |
|---|---|---|
| CN | 201275144 | 7/2009 |
| CN | 104462650 A * | 3/2015 |
| EP | 1166714 | 1/2002 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| JP | 08501477 | 2/1996 |
| JP | 08504333 | 5/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2002051998 | 2/2002 |
| JP | 2002113004 | 4/2002 |
| JP | 2002522106 | 7/2002 |
| JP | 2003511098 | 3/2003 |

(56) References Cited

FOREIGN PATENT DOCUMENTS

| | | |
|---|---|---|
| JP | 2004350702 | 12/2004 |
| JP | 2005536313 | 12/2005 |
| JP | 2006-511296 | 4/2006 |
| JP | 2006511296 | 4/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2014506171 | 3/2014 |
| WO | 9406349 | 3/1994 |
| WO | 9905971 | 2/1999 |
| WO | 200007501 | 2/2000 |
| WO | 200245608 | 6/2002 |
| WO | 2002045608 | 6/2002 |
| WO | 2003026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2014036439 | 3/2014 |
| WO | 2014124231 | 8/2014 |
| WO | 2014130169 | 8/2014 |
| WO | 2015148470 | 10/2015 |
| WO | 2016183285 | 11/2016 |
| WO | 2017192769 | 11/2017 |
| WO | 2017192775 | 11/2017 |

OTHER PUBLICATIONS

Japanese Notice of Allowance dated Jun. 11, 2019 issued in corresponding Japanese Application No. 2018-024907, with English translation.
European Office Action dated Apr. 23, 2018 issued in corresponding European Application No. 07785075.8.
Australian Examination Report dated Jun. 28, 2018, issued in corresponding Australian Patent Application No. 2014318872.
Japanese Notice of Allowance dated Mar. 5, 2019 issued in corresponding Japanese Application No. 2018061040, with English translation.
Japanese Office Action dated Feb. 19, 2019 issued in corresponding Japanese Application No. 2016-558799, with machine translation to English.
Office Action dated Jan. 31, 2018 issued for European Patent Application No. 13763151.1.
Japanese Office Action dated Feb. 16, 2016 issued in corresponding Japanese Application No. 2013-557-926, with English language summary.
Japanese Notice of Allowance dated Jul. 11, 2017 issued in corresponding Japanese Application No. 2013-557-926, with English language summary.
Patent Examination Report No. 2 dated Jun. 14, 2018 in related Australian Application No. 2014214756.
He et al. "An equivalent body surface charge model representing three-dimensional bioelectrical activity" IEEE Transactions on Biomedical Engineering, 42.7 (Jul. 7, 1995) pp. 637-646.
Wolfgang Nolting: Elektrodynamik—Grundkurs Theoretische Physik 3, Springer Spectrum, Feb. 28, 2016, p. 89-91, XP009188752.
European Office Action dated Jan. 28, 2019 issued in corresponding European Application No. 14748567.6.
Australian Office Action dated Jan. 26, 2019 issued in corresponding Australian Application No. 2018211348.
Office Action dated Mar. 17, 2018 issued in corresponding Australian Application No. 2013308531.
Japanese Notice of Allowance dated Feb. 27, 2018 issued in corresponding Japanese Application No. 2015-530101, with English language translation.
Canadian Office Action dated Jan. 22, 2018 issued in corresponding Canadian Application No. 2932956.
Jackson JD, "Classical Electrodynamics", 3rd edition, Dec. 1998, pp. 31-34.
Australian Office Action dated Feb. 26, 2018 issued in Australian Application No. 2017201560.
Extended European Search Report dated Oct. 4, 2018 issued in corresponding European Application No. 16793503.0.
Decision dated Jan. 18, 2018 issued for European Patent Application No. 13176658.6.
Decision dated Jan. 16, 2018 issued for European Patent Application No. 097020945.
Office Action dated Apr. 27, 2016 in corresponding Canadian Application No. 2,747,859.
Christoph Scharft et al. Declaration under 37 C.F.R. 1.132, Nov. 15, 2012.
Canadian Office Action dated Apr. 26, 2017 issued in corresponding Canadian Application No. 2932956.
Canadian Office Action dated Mar. 30, 2017 issued in corresponding Canadian Application No. 2747859.
Canadian Office Action dated Nov. 27, 2017 issued in corresponding Canadian Application No. 2829626.
Chinese Office Action dated Apr. 17, 2017 issued in corresponding Chinese Application No. 201480018328.4.
European Office Action dated Apr. 28, 2014, issued in corresponding European Application No. 09 702 094.5-1660.
European Office Action dated Feb. 29, 2016 issued in corresponding European Application No. 07 785 075.8-1657.
European Office Action dated Mar. 21, 2017 issued in corresponding European Application No. 07785075.8.
Extended European Search Report dated Mar. 14, 2017 issued in corresponding European Application No. EP14843283.4.
Extended European Search Report dated Oct. 18, 2017, issued in European Application No. 15768711.
International Search Report and Written Opinion dated Jun. 26, 2015 issued in International Application No. PCT/US2015/022187.
ISRWO dated Aug. 4, 2017, issued in Application No. PCT/US17/30915.
International Search Report dated Mar. 10, 2015 issued in corresponding International Application No. PCT/US14/54942.
ISRWO dated Sep. 25, 2017, issued in Application No. PCT/US17/30922.
International Search Report dated Apr. 14, 2008 in related International Application No. PCT/CH2007/000380.
Invitation to Pay Additional Fees dated Jan. 8, 2014 in corresponding International Application No. PCT/US2013/057579.
ISRWO dated May 20, 2014 in International application No. PCT/US14/15261.
Japanese Office Action dated Jan. 31, 2017 issued in corresponding Japanese Application No. 2013-557926, with English language summary.
Japanese Office Action dated Jun. 27, 2017 issued in corresponding Japanese Application No. 2015-530101, with English language translation.
Japanese Office Action dated Sep. 26, 2017 issued in corresponding Japanese Application No. 2017-155346, with English translation.
Office Action dated Nov. 7, 2017, issued in European Application No. 15768711.
Office Action dated Oct. 10, 2017, issued in Application No. 2015-557091 with machine translation to English.
Office Action dated Mar. 9, 2016 in corresponding European Patent Application No. 13176658.6.
Office Action dated May 30, 2016 in related Australian Patent Application No. 2012225250.
Office Action dated Oct. 4, 2013 in corresponding Canadian Patent Application No. 2,659,898.
PCT ISRWO dated Jun. 5, 2014, issued in corresponding PCT Application No. PCT/US2013/057579.

(56) References Cited

OTHER PUBLICATIONS

Della Bella et al. "Non-contact mapping to guide catheter ablation of untolerated ventrical tachycardia" European Heart Journal, May 2002, 23(9)742-752.
Examination report dated Jul. 6, 2017 issued in Australian Patent Application No. 2014214756.
Examination Report dated Jun. 27, 2017 issued in Australian Application No. 2013308531.
Examiner's Report dated Dec. 22, 2015 in related Canadian Application No. 2656898.
Extended European Search Report for related Application No. 13176658 dated Sep. 29, 2014.
Extended European Search Report dated Jul. 8, 2016 in related European Application No. 14748567.6.
Gupta et al. "Point of view cardiac mapping; utility or futility? Non-contact endocardial mapping" Indian Pacing and Electrophysiology Journal2:2Q-32 (2002).
He et al. "An equivalent body surface charge model representing three-dimensional bioelectrical activity" IEEE Transactions on Biomedical Engineering, 42.7 (1995) pp. 637-646.
International Search Report and Written Opinion in related Application No. PCT/US2012/028593 dated Mar. 5, 2013.
International Search Report in related Application No. PCT/IB2009/000071 dated Oct. 7, 2009.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Office Action dated Mar. 9, 2016 in corresponding European Patent Application No. 09702094.5.
Partial European Search Report dated Apr. 29, 2014 in corresponding European Application No. 13176658.
Patent Examination Report No. 3 dated Sep. 21, 2016 in related Australian Application No. 2012225250.
Pullan et al. "The inverse problem of electrocardiology" Northeastern University Electrical and Computer Engineering, Feb. 23, 2007.
Van Oosterom A: "Solidifying the solid angle." 2002 Journal of Electrocardiology 2002 vol. 35 Suppl pp. 181-192 ISSN: 0022-0736.
William G. Stevenson et al: "Recording Techniques for Clinical Electrophysiology" Journal of Cardiovascular Electrophysiology. vol. 16 No. 91, Sep. 2005, pp. 1017-1022.
Wolfgang Nolting: Elektrodynamik—Grundkurs Theoretische Physik 3 Springer Spektrum pp. D 89-91.
ISRWO dated Aug. 11, 2016 issued in corresponding International Application No. PCT/US2016/032017.
ISRWO dated Aug. 8, 2016 issued in corresponding European Application No. PCT/US2016/031823.
ISRWO dated Aug. 18, 2016 issued in corresponding International Application No. PCT/US16/32420.
International Search Report and Written Opinion dated Dec. 12, 2017 issued in corresponding International Application No. PCT/US2017/056064.
Canadian Office Action dated Oct. 29, 2018 issued in corresponding Canadian Application No. 2829626.
Japanese Office Action dated Aug. 28, 2018 issued in corresponding Japanese Application No. 2016-542062, with machine translation into English.
Japanese Notice of Allowance dated Sep. 18, 2018 issued in corresponding Japanese Application No. 2015-557091, with English language translation.
Canadian Office Action dated Nov. 7, 2018 issued in corresponding Canadian Application No. 2932956.
Extended European Search Report dated Dec. 5, 2018 issued in corresponding European Application No. 16793622.8.
Japanese Office Action dated Dec. 11, 2018 issued in corresponding Japanese Application No. 2018-024907, with machine translation to English.
Australian Examination Report dated Feb. 8, 2019 issued in corresponding Australian Application No. 2018250516.
European Office Action dated Feb. 6, 2019 issued in corresponding European Application No. 14843283.4.
International Search Report and Written Opinion dated Apr. 8, 2019, issued in corresponding International Application No. PCT/US19/14498.
Japanese Office Action dated Jul. 23, 2019 issued in corresponding Japanese Application No. 2016-542062, with machine translation to English.
International Search Report and Written Opinion dated Jul. 23, 2019 issued in corresponding International Application No. PCT/US2019/031131.
Japanese Office Action dated Oct. 15, 2019 issued in corresponding Japanese Application No. 2018-195960, with machine translation to English.
Extended European Search Report dated Nov. 26, 2019 issued in corresponding European Application No. 19184148.5.
Summons to Attend Oral Proceedings dated Dec. 20, 2019 issued in corresponding European Application No. 13763151.1.
Japanese Office Action dated Jan. 7, 2020 issued in corresponding Japanese Application No. 2016-558799, with machine translation to English.
Australian Office Action dated Jan. 15, 2020 issued in corresponding Australian Application No. 2016262547.
International Search Report and Written Opinion dated Jan. 14, 2020 issued in International Application No. PCT/US2019/060433.

* cited by examiner

CARDIAC VIRTUALIZATION TEST TANK AND TESTING SYSTEM AND METHOD

RELATED APPLICATIONS

The present application claims priority under 35 USC 119(e) to U.S. Provisional Patent Application Ser. No. 62/160,501, entitled "Cardiac Virtualization Test Tank and Testing System and Method", filed May 12, 2015, which is incorporated herein by reference in its entirety.

The present application, while not claiming priority to, may be related to U.S. patent application Ser. No. 14/865,435, entitled "Method and Device for Determining and Presenting Surface Charge and Dipole Densities on Cardiac Walls", filed Sep. 25, 2015, which is a continuation of U.S. Pat. No. 9,167,982 (hereinafter the '982 patent), entitled "Method and Device for Determining and Presenting Surface Charge and Dipole Densities on Cardiac Walls", issued Oct. 27, 2015, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of Patent Cooperation Treaty Application No. CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 14/886,449, entitled "Device and Method For the Geometric Determination of Electrical Dipole Densities on the Cardiac Wall", filed Oct. 19, 2015, which is a continuation of U.S. Pat. No. 9,192,318 (hereinafter the '318 patent), entitled "Device and Method For the Geometric Determination of Electrical Dipole Densities on the Cardiac Wall", issued Nov. 24, 2015, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB09/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to US Design Application Serial No. 29/475,273, entitled "Catheter System and Methods of Medical Uses of Same, Including Diagnostic and Treatment Uses for the Heart", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to U.S. application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/15261, entitled "Expandable Catheter Assembly with Flexible Printed Circuit Board (PCB) Electrical Pathways", filed Feb. 7, 2014, published as WO2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to Patent Cooperation Treaty Application No. PCT/US2015/22187, entitled "Cardiac Analysis User Interface System and Method", filed Mar. 25, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to U.S. application Ser. No. 14/916,056, entitled "Devices and Methods for Determination of Electrical Dipole Densities on a Cardiac Surface", filed Mar. 2, 2016, which is a 35 USC 371 national stage filing of Patent Cooperation Treaty Application No. PCT/US2014/54942, entitled "Devices and Methods for Determination of Electrical Dipole Densities on a Cardiac Surface", filed Sep. 10, 2014, published as WO2015/038607, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

FIELD

The present invention is generally related to systems and methods useful for teaching, testing, and validating surface mapping systems, such as systems and methods used in mapping anatomy or anatomical features of a living being, for example, surface mapping systems and methods used in the diagnosis and treatment of cardiac arrhythmias or other functional and/or structural cardiac abnormalities.

BACKGROUND

The delivery of temporally- and spatially-varying signals to simulate electrophysiological propagation on a defined surface can be challenging in both the complexity of instrumentation and calculation of the driving signal. Approaches to generate the source signal (e.g., dipole, voltage, and/or charge) at the surface, in particular, may require a large number of electrodes to directly deliver source signals or a complex network of nodes to simulate propagation along the surface between sources.

SUMMARY

Using a limited number of electrodes distributed spatially within a test chamber (saline), a set of driving signals can be delivered from the distribution of electrodes that, by superposition of the voltage field generated by each individual electrode, yields a temporally- and spatially-varying field that can be measured and mapped as though the field was generated by actual sources on one or more defined surface to be structurally sampled (surface reconstruction).

In various embodiments, the defined surface(s) can be or represent one or more physical surface of an actual heart or one or more chamber of an actual heart, a virtual surface of an electronic heart model, and/or a combination thereof.

In various embodiments, the physical surface of the actual heart can be taken from a stored version of an actual heart, such as from one or more computer files comprising data representative of the physical and/or functional aspects of the actual heart.

In various embodiments, the heart model can be a representation of a simulated heart, a composite of two or more simulated hearts, a composite of two or more actual hearts, a composite of one or more simulated hearts and one or more actual hearts; a modified actual heart, and/or a combination thereof.

The heart model can represent a properly functioning or abnormally functioning living heart.

In accordance with various aspects of the inventive concept, the limited number of distributed electrodes delivers driving signals that are measured and mapped as a simulation of cardiac activity of a heart, as simulated actual sources, and the defined surfaces can be simulated or representative surfaces of the heart, such as a wall of at least one cardiac chamber.

In accordance with one aspect of the inventive concept, provided is a cardiac virtualization system, comprising: a test tank defining a test volume; a physical heart model disposed within the test tank and representing a heart or at least one heart chamber; a plurality of virtualization electrodes disposed at select locations relative to the physical heart model; and test electronics configured to drive the plurality of virtualization electrodes to generate simulated biopotentials within the test tank as if produced by a heart at the location of the physical heart model.

In various embodiments, the test tank can form an electrically inert fixture that does not conduct or reflect electrical energy.

In various embodiments, the test tank can be made from a material taken from a group consisting of one or more of glass, plastic, resin, Plexiglas, and fiberglass.

In various embodiments, the test volume can be smaller than a volume of the test tank.

In various embodiments, the test volume can be filled with a test fluid that is electrically transmissive.

In various embodiments, the test fluid can be saline.

In various embodiments, the test tank can comprise a plurality of electrode holders configured to secure the virtualization electrodes in place.

In various embodiments, the system can further comprise a support structure configured to hold the physical heart model at a selected position and 3D orientation within the test volume.

In various embodiments, the support structure can include a frame within which the physical heart model is maintained and a base plate that supports the frame.

In various embodiments, the physical heart model can be electrically inert.

In various embodiments, the physical heart model can include a plurality of perforations that enable the test fluid to pass through.

In various embodiments, the physical heart model can be generated by a 3D printer from a heart data file comprising information representing the physical size and shape of a heart or at least one heart chamber.

In various embodiments, the heart data file can be processed by the test electronics to drive the 3D printer to generate the physical heart model.

In various embodiments, the test electronics can drive the plurality of electrodes to generate the simulated biopotentials based on an electrophysiological (EP) model representing the cardiac activity of the heart or at least one heart chamber.

In various embodiments, the heart or at least one heart chamber can be a real heart or at least one heart chamber.

In various embodiments, the heart or at least one heart chamber is a simulated heart or at least one heart chamber.

In various embodiments, the simulated heart or at least one heart chamber includes only simulated heart data.

In various embodiments, the simulated heart or at least one heart chamber includes real and simulated heart data.

In various embodiments, the system can further comprise an actuator configured to move at least a portion of the physical heart model. The movement can simulate the natural movement of heart tissue.

In various embodiments, the actuator can comprise a component selected from the group consisting of: a solenoid, a linear actuator, a piston; a shaped memory component; and combinations thereof.

In accordance with another aspect of the inventive concept, provided is a cardiac virtualization method, comprising: providing a test tank defining a test volume; disposing a physical heart model representing a heart or at least one heart chamber within the test tank; placing a plurality of virtualization electrodes at select locations relative to the physical heart model; and driving the plurality of virtualization electrodes to generate simulated biopotentials within the test tank as if produced by a heart at the location of the physical heart model.

In various embodiments, the test tank can form an electrically inert fixture that does not conduct or reflect electrical energy.

In various embodiments, the test tank can be made from a material taken from a group consisting of one or more of glass, plastic, resin, Plexiglas, and fiberglass.

In various embodiments, the test volume can be smaller than a volume of the test tank.

In various embodiments, the test volume can be filled with a test fluid that is electrically transmissive.

In various embodiments, the test fluid can be saline.

In various embodiments, the test tank can further comprise a plurality of electrode holders configured to secure the virtualization electrodes in place.

In various embodiments, the method can further comprise providing a support structure configured to hold the physical heart model at a selected position and 3D orientation within the test volume.

In various embodiments, the support structure can include a frame within which the physical heart model is maintained and a base plate that supports the frame.

In various embodiments, the physical heart model can be electrically inert.

In various embodiments, the physical heart model can include a plurality of perforations that enable the test fluid to pass through.

In various embodiments, the method can further comprise generating the physical heart model by a 3D printer accessing a heart data file comprising information representing the physical size and shape of a heart or at least one heart chamber.

In various embodiments, the method can further comprise processing the heart data file to drive the 3D printer to generate the physical heart model.

In various embodiments, the method can further comprise driving the plurality of electrodes to generate the simulated biopotentials based on an electrophysiological (EP) model representing the cardiac activity of the heart or at least one heart chamber.

In various embodiments, the heart or at least one heart chamber can be a real heart or at least one heart chamber.

In various embodiments, the heart or at least one heart chamber can be a simulated heart or at least one heart chamber.

In various embodiments, the simulated heart or at least one heart chamber can include only simulated heart data.

In various embodiments, the simulated heart or at least one heart chamber can include real and simulated heart data.

In various embodiments, the method can further comprise providing an actuator configured to move at least a portion of the physical heart model.

In various embodiments, the method can further comprise moving at least a portion of the physical heart model with the actuator. The movement can simulate the natural movement of heart tissue.

In various embodiments, the actuator can comprise a component selected from the group consisting of: a solenoid, a linear actuator, a piston; a shaped memory component; and combinations thereof.

In accordance with another aspect of the inventive concept, provided is a surface mapping systems test, validation, qualification, and teaching apparatus as shown and/or described.

In accordance with another aspect of the inventive concept, provided is a surface mapping systems test, validation, qualification, and teaching method as shown and/or described.

DETAILED DESCRIPTION

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items. And a "combination" of associated listed items need not include all of the items listed, but can include all of the items listed.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Figure 1:
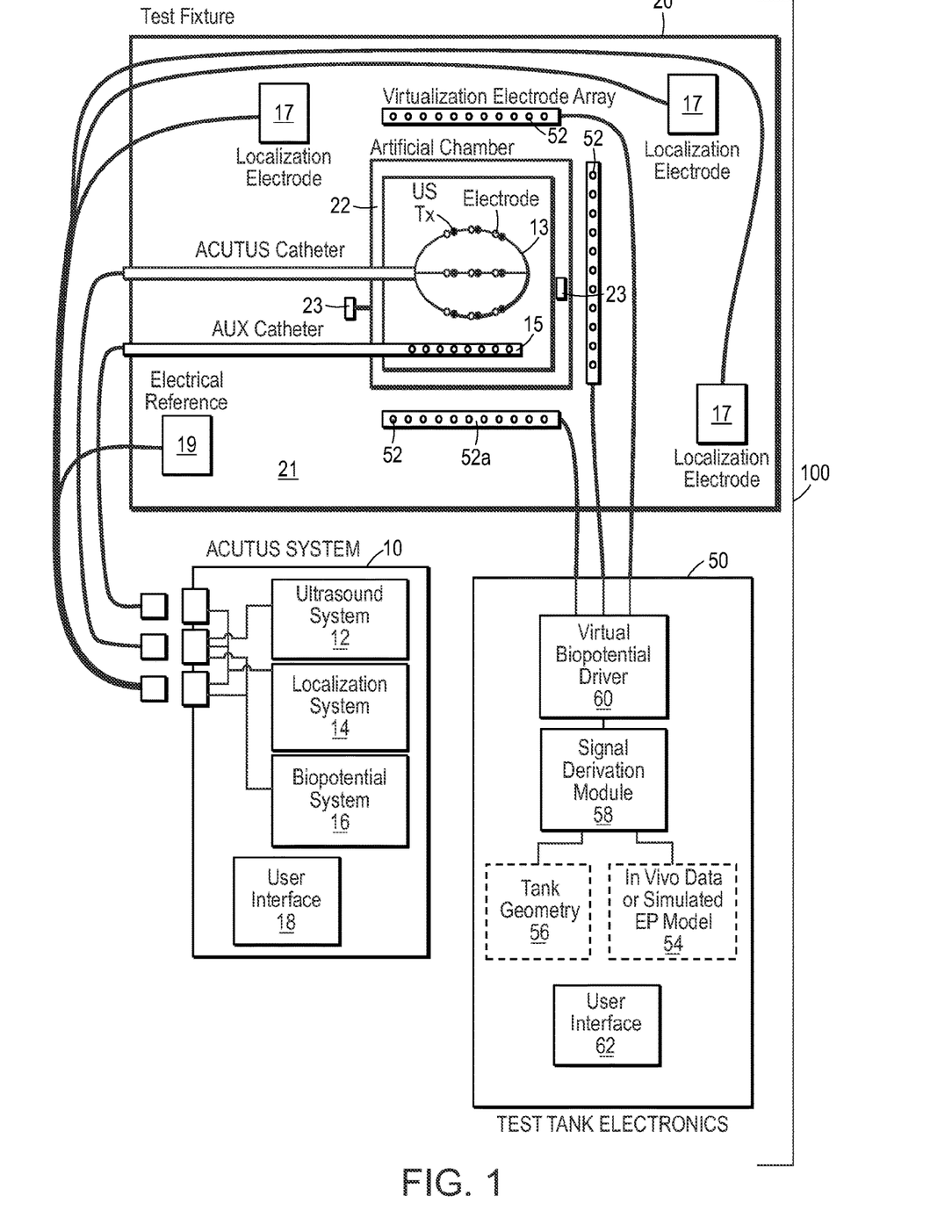
FIG. 1 is a block diagram of an embodiment of a test system in accordance with aspects of the inventive concept.

FIG. 1 is a block diagram of an embodiment of a test system in accordance with aspects of the inventive concept. The test system 100 includes a test tank or fixture 20 and test electronics 50. In conjunction with the test system 100, there is shown a representative cardiac mapping, diagnosis, and/or treatment system, herein representative system 10 configured to map the electrophysiological (EP) activity of a heart or heart chamber. The test system 100 can be used for training, teaching, qualifying and/or validating representative system 10, as examples.

The test tank 20 is a three-dimensional (3D) structure configured to hold an electrically transmissive test fluid, such as liquid saline. Additionally or alternatively, test tank 20 can hold a non-fluidic medium such as a gel. Test tank 20 can also hold one or more objects of varying shapes and/or conductivity, such as objects mimicking a physiological volume. In the depicted embodiment, the 3D shape is a cuboid. In other embodiments, the shape of the test tank could be different, such as a sphere, an ovoid, a spheroid, a cube, a cylinder, or a prism—as non-limiting examples. Beyond these rather standard 3D shapes, the test tank 20 could take other 3D shapes, such as custom or irregular shapes.

In this embodiment, the test tank 20 is sized and shaped as a cuboid that generally approximates the shape of a torso, such as a human torso. As examples, the test tank 20 could be sized and shaped to approximate a human male torso, a smaller human female torso, or a human child torso, and so on. In still other embodiments, the test tank could be shaped like the torso itself.

The environment created within the test tank 20 is intended to replicate and approximate one or more characteristics of the environment within a body, so that effective teaching, testing, and validating of cardiac mapping, diagnostic, and treatment systems can be conducted within the test tank 20. In some embodiments, test tank 20 comprises one or more minimally-conductive or non-conductive components (e.g. one or more components constructed and arranged to simulate a heart surface, such as physical heart model 22, and/or other components of or objects within test tank 20). In these embodiments, test tank 20 can additionally comprise one or more components that include conductive materials, such as surface patches or other electrodes. As examples, the minimally-conductive or non-conductive (hereinafter minimally conductive) materials forming the test tank 20 can include glass, plastic, resin, Plexiglas, fiberglass, and/or any number of other materials that are minimally-conductive (e.g. to avoid reflecting or conducting electrical energy). Alternatively or additionally, materials forming test tank 20 can be constructed and arranged to provide a watertight barrier. The test tank 20 can be filled with test fluid 21 that is at least somewhat conductive (e.g. conductive to signals in frequency ranges below 100 KHz), such as when test fluid 21 comprises buffered saline with a conductivity relatively equivalent to human blood.

A physical model of a heart is disposed in the test tank 20 and submerged within the test fluid 21, referred to as physical heart model 22 in FIG. 1. In FIG. 1, the physical heart model 22 is depicted as a square for simplicity. But the physical heart model 22 can be provided in a form that simulates the geometry of at least a portion of a real heart (e.g., a human heart or pig heart). That is, the physical heart model 22 could be a physical model of a complete heart, a single heart chamber (e.g. the left atrium), or of multiple heart chambers (e.g., one or more of the left atrium (LA), right atrium (RA), left ventricle (LV), and right ventricle (RV)). In some embodiments, test system 100 comprises one or more actuators 23 positioned to cause movement of one or more portions of physical heart model 22, such as to simulate a beating heart or otherwise simulate cardiac wall motion. In some embodiments, one or more actuators 23 comprise a component selected from the group consisting of: a solenoid, a linear actuator, a piston; a shaped memory component; and combinations thereof. In some embodiments, one or more actuators 23 are operably attached to a wall portion of physical heart model 22 stabilized by fixation to one or more portions of test tank 20, such that activation of actuator 23 causes motion of the wall portion of physical heart model 22 relative to test tank 20. In some embodiments, one or more actuators 23 are positioned within a wall portion of physical heart model 22, such that activation of the actuator 23 causes motion of one wall portion relative to another wall portion of physical heart model 22. In some embodiments, multiple actuators 23 are operably attached to multiple wall portions of physical heart model 22, such as to simulate at least some of the muscular contractions of a beating heart. In some embodiments, the driven motion of a wall of the physical heart model 22 can be synced with a cardiac signal being simulated within test tank 20, as described herein. The physical heart model 22 can additionally include adjacent or connected anatomical structures, such as veins (e.g. pulmonary veins), airways, organs, etc. The physical heart model 22 and/or tank 20 can further include one or more valves or other flow generators, configured to generate flow patterns within the physical heart model 22, such as flow patterns intended to simulate flow patterns within a living heart and/or heart chamber. In some embodiments, test system 100 does not include physical heart model 22, such as when test system 100 is configured to simulate cardiac electrical activity without including a cardiac surface positioned within test tank 20. In some embodiments, physical heart model 22 comprises one or more materials (e.g. one or more minimally conductive materials) constructed and arranged to simulate at least a portion of one or more lungs. In some embodiments, physical heart model 22 comprises one or more materials configured to distort field lines, such as one or more conductive materials constructed and arranged to simulate distortion caused in-vivo by one or more veins. In some embodiments, heart model 22 comprises a material selected from the group consisting of: an electrically non-conductive material; an electrically conductive material; electrically conductive silicone; electrically conductive foam; glass; plastic; resin; carbon fiber; 3D printable conductive plastics; and combinations of two or more of these.

In one embodiment, the physical heart model 22 is a static model that represents the physical structure of a heart, but not the heart's functioning (e.g. does not change shape to simulate the contractions and other wall motion of a beating heart). The physical heart model 22 can be a physical representation of a real heart or a simulated heart for which corresponding biopotential data is also stored (e.g. data to be simulated as described herein). In another embodiment, the physical heart model 22 can be a functional model, capable of simulating the wall motion of a beating heart. In some embodiments, the physical heart model 22 is electrically inert, that is, electrically nonconductive and/or electrically transparent. In another embodiment, the physical heart model 22 can mimic an actual conductivity distribution of the tissue being simulated, and/or can have an anisotropic conductivity distribution. The conductivity distribution can be known by system 100 and used in calculation of simulated electrical signals within test tank 20.

The physical heart model 22 can comprise a known shape and dimensions, which can be represented in an electronic data file used by the test electronics, as discussed in more detail below. The physical heart model 22 can contain a plurality of perforations that allow the test fluid 21 to flow through the physical heart model 22, while maintaining the overall shape, surfaces, and contours of the heart being represented by the physical heart model 22. In some embodiments, the physical heart model 22 is acoustically reflective so that ultrasound devices and systems can be effectively used (e.g. tested) therewith. In some embodiments, the physical heart model 22 is constructed of an acoustically reflective material. In some embodiments, the physical heart model 22 is treated and/or coated with an acoustically reflective material that may be adhered, laminated, layered, pinned, clipped and/or clamped to the physical heart model 22, such as a gel, spray, epoxy, and the like. In some embodiments, the physical heart model 22 contains a plurality of perforations, the density of which are not limiting to the reflectivity of ultrasound signals from the surface. In some embodiments, the physical heart model 22 includes a surface texturing treatment, additive, coating, or the like, which changes the specular or reflective profile of the material.

Test system 100 can comprise a plurality of virtualization electrodes 52 provided and arranged to deliver electrical signals into the test tank 20 environment that mimic biopotentials generated by a heart, as if generated by the physical heart model 22 (i.e. simulated biopotentials present on the surface of heart model 22).

The test electronics 50 can include one or more computer processors and memory circuitry configured to store and process information used to operate the test system 100, including simulating a functioning heart within the test tank 20.

In this embodiment, the test electronics 50 has stored and/or can electronically obtain heart data 54. The heart data 54 can include physical data that describes the physical attributes and features of a heart, whether a real heart or a simulated heart, such as when geometric or other values used to virtually recreate the heart or aspects thereof (e.g., surfaces, chambers, wall motion, etc.) are known and/or determinable. A simulated heart can include a mix of real heart data (e.g. previously recorded heart data) and simulated heart data, or just simulated heart data. The heart data 54 can, in some embodiments, enable production of the physical heart model 22, such as by 3D printing, if the physical heart model 22 is not preexisting.

The heart data 54 can further include electrophysiological (EP) data representing the electrical activity and/or other functioning of a heart (e.g. the heart represented by the physical heart model 22). The EP data can be actual EP data recorded from a real heart and/or simulated EP data generated for a simulated heart, in either case stored as an EP model. The EP model, therefore, can include data recorded from an actual beating heart to be reproduced, simulated data, or combinations thereof.

The test electronics 50 also includes test tank 20 geometry information 56, including dimensions of the test tank 20, used to establish a 3D frame of reference with respect to the test tank 20. The tank geometry information 56 can include the position and orientation of the physical heart model 22 within the 3D frame of reference and the location of each virtualization electrode 52 within the 3D frame of reference. The position of each virtualization electrode 52 within the test tank 20 is known. Therefore, the locations of the virtualization electrodes 52 relative to test tank 20 and/or the physical heart model 22, and surfaces thereof, are also known or determinable by the test electronics 50. In some embodiments, catheter 13 of representative system 10, in conjunction with the localization electrodes 17 of system 100, can be used to estimate and/or confirm the relative positions of electrodes 52 and/or the surface of the physical heart model 22 within tank 20 (i.e. with respect to the localization electrodes 17).

The test electronics 50 can include a signal derivation module 58 that receives and processes the heart data 54 and tank geometry information 56 to drive the virtualization electrodes 52, via a virtual biopotential driver 60, to simulate a functioning heart in the test tank 20, whether a real heart or a simulated heart. The functioning of the heart is determined from the EP model, which is used to drive the virtualization electrodes 52 via the virtual biopotential driver 60. This configuration causes the virtualization electrodes 52 to deliver a series of voltages into the test tank 20 that simulate the voltages generated by a simulated heart, such as if the simulated heart was of the same geometry and position of the physical heart model 22 in the test tank 20. That is, in some embodiments, potentials applied to one or more virtualization electrodes 52 produce corresponding potentials on a surface of a simulated heart represented within test tank 20 (e.g. on the surface of physical heart model 22), such that the corresponding potentials have the same electrical characteristics, including magnitude, as potentials that would be created by charge sources of the simulated heart. Additionally, virtualization electrodes 52 can be driven to simulate one or more electrical "artifacts" in tank 20, such as artifacts encountered during a clinical procedure from patient respiration.

Electrodes 52 can be configured as voltage sources and/or current sources.

The signal derivation module 58 is configured to calculate the signals to drive the virtualization electrodes 52 in accordance with the desired EP model. The EP model can represent the EP aspects of the heart as dipole or surface charge densities, as described in U.S. Pat. Nos. 8,918,158 and 8,700,119. In such cases, the signal derivation module 58 can be configured to calculate a forward and/or an inverse solution (from dipole density or surface charge density information) to determine electrical potentials to be output from the virtualization electrodes 52. See also Signal Derivation for Tank Virtualization below. In some embodiments, the signal derivation module 58 can calculate the electrical potentials using a computational model (e.g. FEM, BEM, or an analytical solution) for the field propagation configured to account for the conduction distribution of the material(s) used to create the physical heart model 22.

The virtual biopotential driver 60 can act as a current and/or voltage driver, to independently drive each virtualization electrode 52 based on signal derivation module 58 to produce a desired field in test tank 20 corresponding to the desired EP model (e.g. an EP model based on the physical heart model 22).

The EP model can cause the virtual biopotential driver 60 to drive the virtualization electrodes 52 to produce potentials representing specific arrhythmias, healthy patterns, abnormalities, and so on in cardiac electrical activity. The EP model can include electrical activity of a simulated heart comprising one or more chamber, and the virtualization electrodes 52 can be driven to simulate electrical activity present on the surface of the corresponding one or more chambers. In these embodiments, a physical heart model 22 can be included in test system 100, and the physical heart model 22 can comprise an associated one or more chambers.

In some embodiments, the EP model could be dynamic so that it is responsive to changes, such as by activity of the system 10. That is, the test system 100 could allow for simulated ablations by system 10 and accordingly modify the EP model signals driving the virtualization electrodes 52 based on the ablations performed.

As discussed above, the virtualization electrodes 52 can provide voltage signals that propagate through the test fluid 21 in the test tank 20 and represent biopotentials of a simulated heart. The voltages output by these virtualization electrodes 52 simulate and/or approximate voltages generated from a beating heart, while the test tank 20 simulates and/or approximates a human torso containing the beating heart. The virtualization electrodes 52 are driven by the test electronics 50 based on stored cardiac information associated with a stored heart model (e.g. a stored heart model upon which a physical heart model 22 is based).

The virtualization electrodes 52 can be provided as one or more virtualization electrode arrays; and each array can form a grouping of two or more electrodes. In FIG. 1, three virtualization electrode arrays are shown, each including a plurality of virtualization electrodes 52 disposed on a substrate 52a. Other virtualization electrode arrays can be present, but not visible in the figure. And electrode arrays can take other forms not shown. In one embodiment, six (6) linear arrays comprising twenty four (24) total electrodes (e.g., four electrodes per array) can be used. The single row, linear virtualization electrode arrays 52 shown in FIG. 1 are non-limiting examples. In some examples, one or more matrices of virtualization electrodes 52 can be used, such as an array with rows and columns of electrodes. In some embodiments, one or more virtualization electrodes or virtualization electrode arrays 52 can repositioned (e.g. rotated). In some embodiments, one or more single virtualization electrodes 52 are individually positioned. The position of one or more virtualization electrodes 52 can be selected to enable complex electrical field generation not otherwise enabled with alternate positioning of the one or more virtualization electrodes 52.

In various embodiments, the virtualization electrodes 52 can be used to simulate biopotentials generated on an endocardial (inner) surface and/or an epicardial (outer surface) of a simulated heart. Endocardial surfaces are defined by each heart chamber, while epicardial surfaces are defined by the entire heart muscle. For example, in one embodiment the virtualization electrodes 52 are driven to simulate biopotentials generated on one or more simulated cardiac locations: such as endocardial surfaces, epicardial surfaces and/or any cardiac location (e.g. within a cardiac wall). In some embodiments, the virtualization electrodes 52 are driven (e.g. as determined by signal derivation module 58) by virtual biopotential driver 60 to simulate a surface charge density and/or dipole density pattern present on an epicardial and/or endocardial surface. In some embodiments, the virtualization electrodes 52 are driven to simulate charge sources originating under a cardiac surface (i.e. within an internal location of the heart wall).

In some embodiments, one or more of the virtualization electrodes 52 can be made from or comprise Ag/AgCl. Alternatively or additionally, one or more of the virtualization electrodes 52 is made from or comprise gold, platinum, and/or stainless steel. In some embodiments, specific sizes and shapes of electrodes could be used to generate different electrical effects (e.g. different simulated biopotential patterns). In some embodiments, the electrodes are circular.

The virtualization electrodes 52 are positioned within the test tank 20 relative to one or more simulated heart chambers (e.g. when a physical heart model 22 is included comprising a corresponding one or more heart chambers). In some embodiments, virtualization electrodes 52 can be positioned relative to one simulated heart chamber, and subsequently repositioned to be relative to a second simulated heart chamber.

The test system 100 can further include a user interface module 62, which can provide various user input and output devices. Input devices can include, but are not limited to, one or more of a keyboard, mouse, touchscreen, buttons, switches, dials, camera, microphone, electronic receiver, and so on. The output devices can include, but are not limited to, one or more of a display screen, touchscreen, speaker, LEDs, printer, electronic transmitter, and so on.

In various embodiments, the user interface module 62 can be used to select: a tank geometry, a desired EP model, a simulated heart, and/or a cardiac condition (e.g. an arrhythmia), and/or to otherwise control outputs. In various embodiments, the user interface module 62 can be used to modify parameters of test tank 20, as well as start and/or stop operation of the test system 100.

The test system 100 is configured to simulate the electrical activity of a beating heart so that the mapping, diagnostic, and/or treatment capabilities of the representative cardiac mapping, diagnosis, and/or representative system 10 can be demonstrated, tested, qualified, and/or validated. In FIG. 1, the representative system 10 includes a cardiac mapping system, and it can include other functional elements. The representative system 10 can include an ultrasound system module 12 that drives associated components of a mapping catheter 13. The mapping catheter 13 is shown as including a basket array that could be placed in the left atrium, as an example, but other types of mapping catheters could be used. For example, the basket array could be placed in the left atrium of the physical heart model 22 in the test tank 20 and then operated to map the simulated cardiac activity in the test tank 20. In this embodiment, the basket array includes a plurality of splines, each including pairs of electrodes (e.g. electrical recording electrodes) and ultrasound (US) transceivers. Three such pairs are shown on each spline in FIG. 1, but this embodiment is merely shown as a non-limiting example.

A localization system module 14 can be included in system 10, and configured to localize (i.e. determine the position of) one or more devices, such as mapping catheter 13, auxiliary catheter 15 (described herebelow), or another device (e.g. another device of system 10).

The localization system module 14 can drive a set of localization electrodes of test system 100, localization electrodes 17, which are positioned and spaced within the test tank 20 to approximate anatomically relevant positions on a torso, (e.g. relative to the position of a simulated heart and/or physical heart model 22). Localization electrodes 17 can be provided in pairs, all of which are not visible in FIG. 1. In some embodiments, there are six (6) localization electrodes 17 (e.g. three (3) pairs). Electrodes 17 in a pair tend to be on opposite sides of the torso and tend to be configured to communicate with each other, but not with other electrodes 17. In such an embodiment, an X pair simulates locations under the armpits, a Y pair simulates locations at the low back and high chest, and a Z pair simulates locations at the high back and low chest. The localization electrodes 17 can be made from or comprise Ag/AgCl, as one example. In some embodiments, system 10 comprises a set of localization electrodes similar to localization electrodes 17 of test system 100, but configured for application to the torso of a real patient.

In order to perform a localization, the electrodes of mapping catheter 13 can record a voltage based on a signal applied between two localization electrodes 17 (e.g. a constant or varying voltage applied between two localization electrodes 17), and the recorded voltage can be used to determine the position and/or orientation of a portion of the mapping catheter (e.g. the position of the recording electrode). In some embodiments, test system 100 further comprises an auxiliary catheter 15, such as a catheter configured to ablate tissue (e.g. with electrical energy; cryoenergy; ultrasound energy; laser energy; and/or chemical energy), and including one or more electrodes configured to record a voltage based on a signal applied between two localization electrodes 17 as described hereabove. Auxiliary catheter 15 can be configured to help orient mapping catheter 13. In some embodiments, auxiliary catheter 15 comprises a second mapping catheter, such as a lasso catheter. In some embodiments, auxiliary catheter 15 is configured to provide contact electrogram mapping.

The localization system module 14 can also drive an electrical reference electrode 19 of test system 100, which serves as an analog ground. The electrical reference electrode 19 can be located at an anatomically relevant position and can be configured and arranged to simulate a reference patch, or catheter, or both (e.g. a reference patch and/or catheter of system 10). In some embodiments, reference electrode 19 can be distributed, such as to affect the field pattern generated by system 100 and further allow more complex fields to be generated. For example, Laplacian electrode like arrangements of electrodes 52 and electrical reference electrode 19 can provide focus regions in the field pattern generated.

A biopotential system module 16 can be included to drive and process information and data from the system 10 catheters (e.g. mapping catheter 13 and/or auxiliary catheter 15).

In this embodiment, the mapping catheter 13 and auxiliary catheter 15 connect to the representative system 10 as they would for normal operation (e.g. a mapping procedure on a human patient). However, the localization electrodes 17 and reference electrode 19 take a form intended for the test tank 20, which can be different from the adhesive-backed patch electrodes normally used with a living being. However, the localization electrodes 17 and reference electrode 19 can connect to the same localization electrode ports in the representative system 10 as would the more typical adhesive localization electrodes and reference electrode used on a living being. The test tank electrodes 17, 19 replace actual patch electrodes placed on the body during clinical procedures, but the representative system 10 otherwise runs normally. In some embodiments, system 10 is configured to test one or more portions of test system 100, such as when system 10 is configured to analyze test electronics 50 (e.g. to allow data feedback) or another component of test system 100.

The representative system 10 can also include a user interface module 18 for user interaction with the representative system 10, which can include input and output devices as described above. The representative system 10 can be a non-contact mapping system, in which case an inert heart provides no bar to the intended result. However, other systems are contact mapping systems, where a mapping catheter touches a wall to determine its location for mapping. On contact, such systems detect changes in the measured voltage signal that indicates that a wall has been touched. In various embodiments, the test system 100 can be adapted to work with contact mapping systems. For example, the test system 100 could track a catheter tip (e.g. a mapping catheter tip) in 3D and, since the wall locations are known, the test system 100 can inform the catheter or representative system 10 (e.g. via a signal coupled into a data signal of the catheter or system) when the catheter tip is on the wall (even though wall is inert). In another embodiment, surfaces of the physical heart model 22 can be connected to a voltage source (e.g. a DC voltage source) that causes a sufficient electrical signal in response to contact. In still other embodiments, surfaces of the physical heart model 22 can include insulated switches that send a signal upon contact and/or depression with the surface of physical heart model 22. There are various manners for making the otherwise inert physical heart model 22 responsive to contact mapping electrodes.

Figure 2:
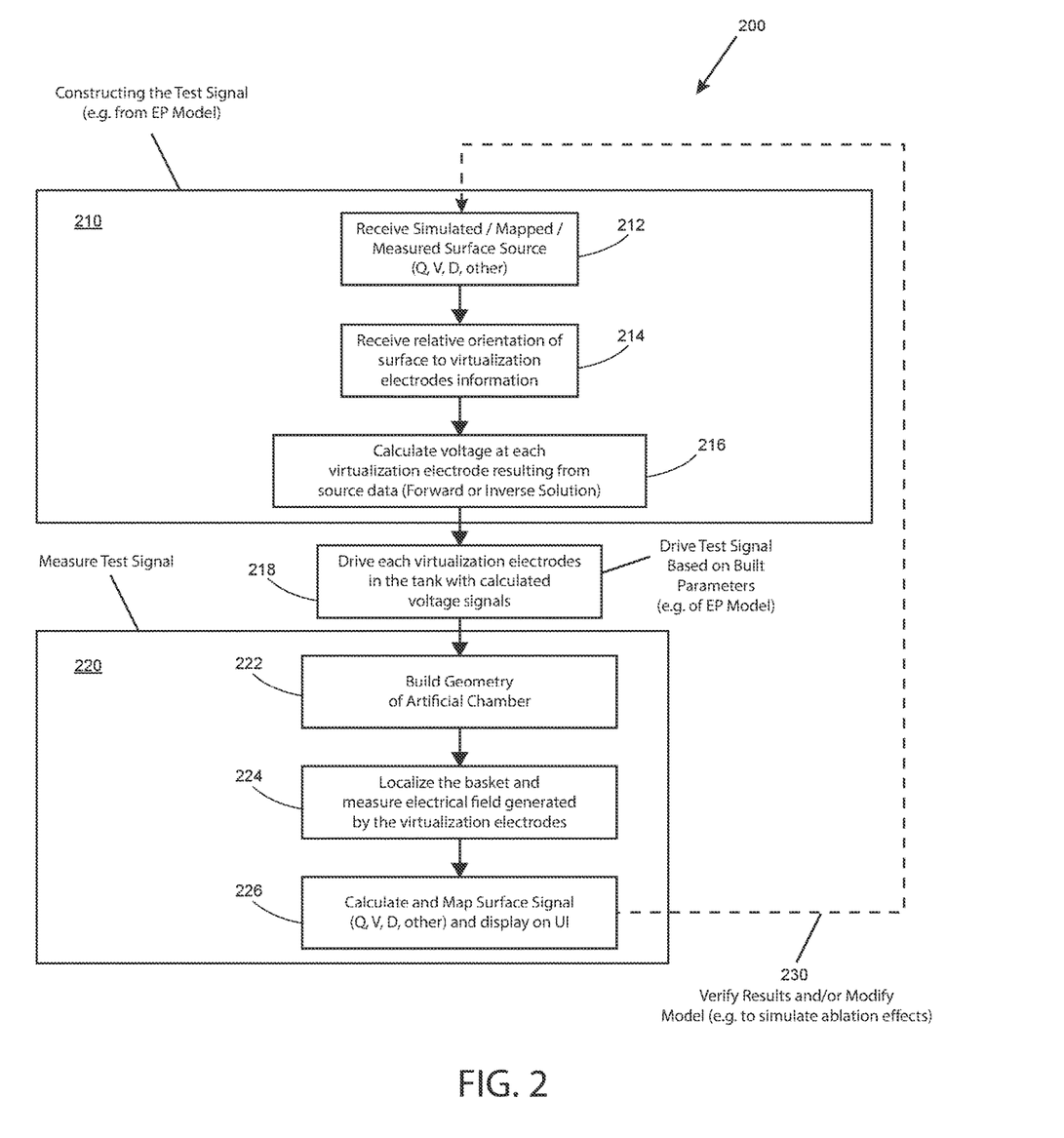
FIG. 2 provides a flowchart of an embodiment of a method of test system signal generation, in accordance with aspects of the inventive concept.

FIG. 2 provides a flowchart of an embodiment of a method 200 of test system signal generation, in accordance with aspects of the inventive concept. Method 200 can be implemented, for example, by the test system 100 of FIG. 1.

A first set of steps 210 relate to constructing a test signal used to drive the virtualization electrodes 52. In a first step 212, the signal derivation module 58 receives simulated, mapped, and/or measured surface source information (charge density, dipole density, voltage, and so on), which forms the EP model part of the heart data 54. In another step 214, the signal derivation module 58 receives information providing a relative orientation of heart chamber surfaces with respect to the virtualization electrodes 52. Based on the foregoing, in step 216, the signal derivation module 58 calculates voltage signals to be output at each of the virtualization electrodes 52. In some embodiments, signal derivation module 58 calculates these voltage signals based on processing dipole density or surface charge density information using forward to inverse solutions, as appropriate.

In step 218, the virtual biopotential driver 60 drives the virtualization electrodes 52 according to the calculated voltage signals.

A second set of steps 220 measure the voltages generated by the test system 100 to map at least one surface of a heart represented by the physical heart model 22 and EP model used to generate the voltages. This can be accomplished according to normal operation of the representative system 10. Alternatively, a simulated heart surface is used (e.g. when test system 100 does not include physical heart model 22).

In step 222, a geometry of the physical heart model (or artificial chamber) 22 is built using the ultrasound electrodes. In alternative embodiments, a pre-determined surface is included in test system 100 (e.g. when test system 100 does not include physical heart model 22 and/or when system 10 does not include ultrasound electrodes or other geometry gathering sensors. In step 224, the mapping catheter 13 is localized, and the electric field generated by the virtualization electrodes 52 is measured by the mapping catheter 13. In some embodiments, the electric field generated by virtualization electrodes 52 is measured by auxiliary catheter 15. Based thereon, in step 226, the representative test system 100 biopotential system module 16 calculates and maps a surface signal (charge density, dipole density, voltage, and so on), which can be output (e.g., displayed) via user interface module 18.

An optional step 230 can be configured to verify the results and/or modify the EP model and, therefore, the outputs from the virtualization electrodes 52, can be modified (e.g. as described hereabove in reference to FIG. 1). For example, a module can be provided (e.g., in the test system 100) that compares the original EP model with the data from step 226 to determine that sufficiency of operation of the representative system 10 is present. As another example, if the representative system 10 includes an ablation catheter (e.g. as an auxiliary catheter 15), an ablation can be simulated and the EP model adjusted as if the ablation had taken place (e.g. removal, reduction or other modification of signals present at surface locations where the simulated ablations occurred). This ablation simulation would cause a revised set of voltages to be output by the virtualization electrodes 52 in step 218. As a result, a different mapping would be output in step 226.

In some embodiments, the physical heart model 22 could be responsive to an ablation output from an ablation catheter to automatically adjust the EP model processed by the virtual biopotential module 60.

Figure 3:
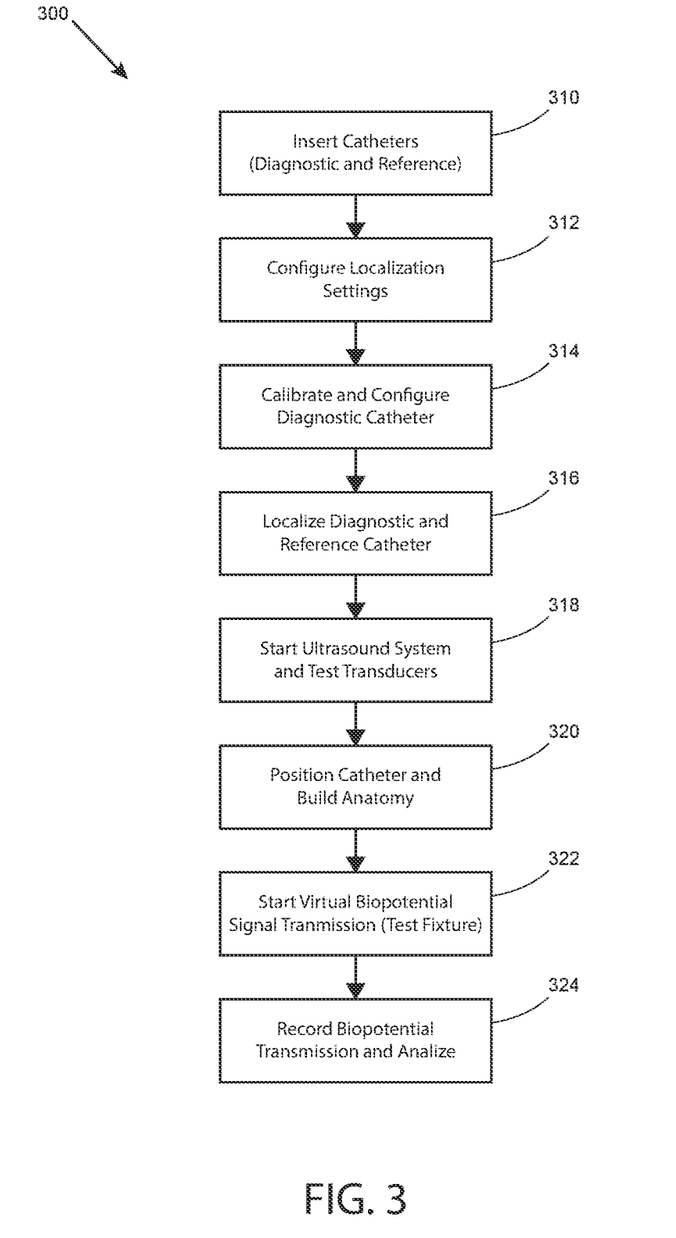
FIG. 3 provides a flowchart of an embodiment of a test system method, in accordance with aspects of the inventive concept.

FIG. 3 provides a flowchart of an embodiment of a test system method 300, in accordance with aspect of the inventive concept. The method presumes that the test tank 20, with virtualization electrodes 52, is provided and arranged for use with a representative system 10. In some embodiments, test system 100 further includes physical heart model 22.

In step 310, mapping catheter 13 and/or auxiliary catheter 15 are appropriately placed in the test tank 20 and/or physical heart model 22. Localization electrodes 17 and/or reference electrode 19 are positioned or are already in an appropriate position.

In step 312, the localization settings are configured. In this step, locations of the tank localization electrodes 17 are determined and recorded. Electrodes on the mapping catheter 13 and/or auxiliary catheter 15 are determined and recorded.

In step 314, the diagnostic catheter, here mapping catheter 13, is configured and calibrated by system 10. This step can include removing electrodes with inadequate signal quality by turning "off" such electrodes (e.g. via a user interface module of system 10) as a way to tell system 10 to ignore the electrodes with inadequate signal quality.

In step 316, localizing the diagnostic (mapping) catheter 13 and/or auxiliary catheter 15 are performed. This step can include the representative system 10 localizing each electrode of these catheters according to its own algorithms for fitting signals to the associated catheter shape.

In step 318, the ultrasound system and transducers on the basket array of mapping catheter 13 are activated. This step can include checking the ultrasound transducers for malfunctions, turning "off" bad transducers (e.g. via a user interface module of system 10 as a way to tell system 10 not to use the bad transducers), and/or verifying that the ultrasound transducers are responsive by turning on the ultrasound system and moving the mapping catheter 13 to make sure that recorded signals are changing.

In step 320, the mapping catheter 13 can be positioned in the physical heart model 22, and an anatomy of the physical heart model 22 can be built. This step can include choosing a starting position preferably in the center of the physical heart model 22 and building the anatomy using localization and ultrasound ranging using the representative system 10's native capabilities. The building of the anatomy can be performed until the anatomy "looks good" to the user, e.g., via a display screen, and/or until a quantitative measure of acceptability has been reached (as determined by one or more algorithms of system 10).

In step 322, the virtual biopotential signal transmission from the virtualization electrodes 52 is begun by the test system 100, according to the appropriate EP model.

In step 324, the representative system 10 records the simulated biopotential transmissions, which can then be analyzed by system 10. This step can include the representative system 10 recording the output biopotential and calculating the surface signals (e.g. voltage, surface charge density and/or dipole density) for display via the user interface module 18.

Signal Derivation for Tank Virtualization

Problem

Producing a temporally-varying and spatially-varying (e.g. propagating) signal along a surface with correlation to true cardiac electrophysiology is very challenging. Delivery of "perfect" waveform morphologies (R, RS, S) on a set of electrodes is more likely to yield "flashing spots" than a smooth propagation of voltage change along the surface. An empirical approach to vary the amplitude, duration, and phase of ideal signals to produce an accurate representation of in vivo electrophysiological signals can be challenging.

Background

Using a tank/electrode setup with a set of distributed electrodes (e.g. virtualization electrodes 52 described hereabove) positioned around a measurement device (e.g. mapping catheter 13 described hereabove) with an optional cardiac chamber surface model, the distributed electrodes can be driven with a set of signals such that the superposition of voltage fields produced by each individual electrode yields a net temporally-varying and spatially-varying field that can be measured by the sensing device and mapped back to an accurate representation of an electrophysiological activation pattern on a defined surface. The derivation of the signals delivered by the distributed driving electrodes is critical in deterministically re-creating the electrophysiological activation pattern.

Solution

Figure 4:
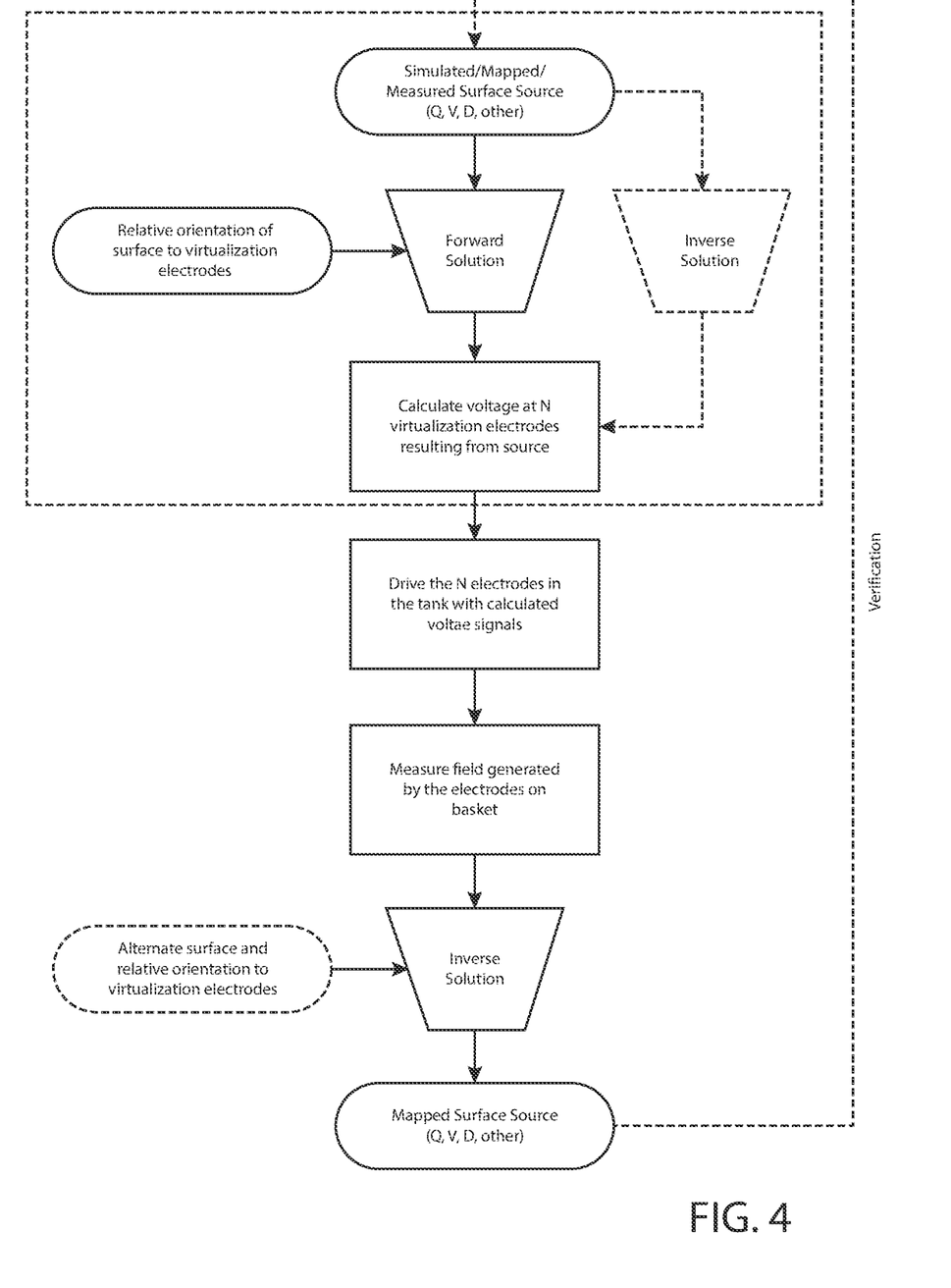
FIG. 4 provides a general block diagram of an embodiment of a virtualization method, in accordance with aspects of the inventive concept.

A general block diagram of an embodiment of a virtualization method is provided in FIG. 4. The section pertaining to the derivation of driving signals is highlighted by the dashed box shown.

As outlined in the flowchart embodiment of FIG. 4, the set of signals delivered by the driving electrodes (e.g. virtualization electrodes 52 described hereabove) can be derived using the following:

1) A source model for the surface sources (charge/dipoles) or the resultant surface voltage.
2) A defined surface on which sources exist (e.g. an endocardial surface of the left atrium or other cardiac chamber surface)

a. Ideal/simulated—e.g., sphere or ellipsoid
b. Reconstructed/imaged/traced—e.g. system 10 described hereabove
c. Electrodes of the measurement device (e.g. mapping catheter 13 described hereabove)—this could be used to generate a dataset from measured in vivo data, but will likely limit the complexity of the producible activation pattern.
3) An activation pattern of the sources on the surface
   a. Mapped—inverse or forward mapped (e.g. by system 10 described hereabove)
   b. Measured/sampled—contact map, possibly interpolated (e.g. by a contact mapping system)
   c. Simulated—propagation or action potential model or FEM model
4) Relative position/orientation of the driving electrodes to the surface.
5) Inverse solution or forward calculation from the surface sources to the driving electrodes.

Test Tank

Figure 5:
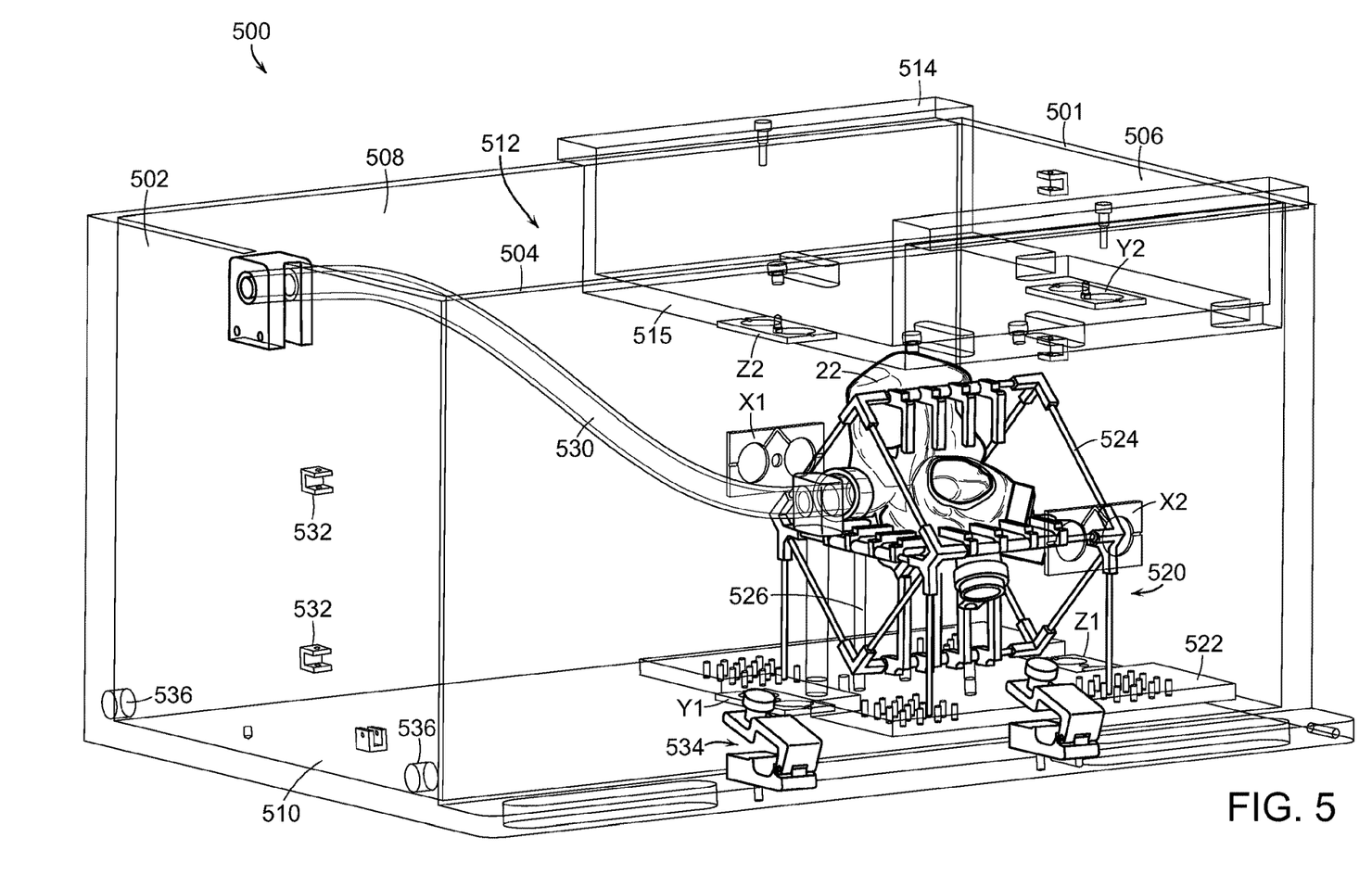
FIG. 5 shows an embodiment of a test tank design, in accordance with aspects of the inventive concept.

FIG. 5 shows an embodiment of a design of a test tank 500, in accordance with aspects of the inventive concept, such as test tank 20 above. The test tank 500 defines a test volume within which a body, a portion of a body, and/or a cavity of a body can be simulated or otherwise represented. The test tank 500 can take a number of different forms and shapes, as discussed above. In a presently preferred embodiment, the test tank has a cuboid shape, but the inventive concept is not so limited.

Materials used to form all or portions of the volume can be electrically inert, such as being substantially, if not completely, electrically non-conductive and substantially, it not completely, non-reflective with respect to electrical energy. Examples of types of materials that can be used are discussed above. And as discussed above, the test tank 500 is filled with a test fluid 21 (e.g. an electrically conductive fluid and/or an ultrasonically transmissive fluid).

In this embodiment, the test tank 500 includes four sides 502, 504, 506, and 508 and a bottom 510, which cooperate to define test volume 512 therein. A 3D frame of reference can be physically and/or virtually (e.g., by the test electronics 50) defined within the test volume 512. The test volume 512 used for cardiac virtualization need not include the entire volume of the test tank 500. Within the test volume 512, a support structure 520 is disposed. The support structure 520 is configured to support the physical heart model 22, and maintain the physical heart model 22 in a selected orientation. The support structure can be integral with the tank bottom 510 or it can be a separate apparatus disposed on top of the tank bottom 510. If a separate apparatus, the support structure 520 can be permanently, semi-permanently, or freely removable from the tank bottom. In any case, the support structure 520 is configured to maintain the physical heart model is a selected position and orientation within the 3D frame of reference.

To facilitate the foregoing, the support structure 520 can include a base plate 522, a frame 524, and one or more stanchions 526 that support the frame 524 with respect to the base plate 522. The physical heart model 22 can be held by and secured within the frame 524 and maintained on the base plate 522 so that it is preferably surrounded by test fluid (e.g. test fluid 21 described hereabove) within the test tank 500, in the present embodiment.

The test tank 500 can further include a cover 514. The cover 514 can be made from the same types of electrically inert materials as the test tank sides 502, 504, 506, and 508. In this embodiment, the cover 514 has a depressed surface 515 disposed below a top rim 501 of the test tank 500. In this embodiment, the test tank further includes one or more ports, such as the two ports 536 shown, used to fill and/or drain test tank 500.

In this embodiment, localization electrode holders are shown, and configured to hold localization electrodes 17 discussed above. In this embodiment, there are three (3) pairs, for six (6) total localization electrodes. There is an X pair X1, X2, a Y pair Y1, Y2 and a Z pair Z1, Z2. As discussed above, these electrode pairs simulate or approximate patch electrodes placed at different locations on the body (e.g., at different locations of the torso). Generally, it is preferred that electrodes in a pair are opposite each other, with the physical heart model 22 at least partially between the paired electrodes, as shown in FIG. 5. In this embodiment, the Y2 and Z2 electrodes are attached to the top cover 514. The test volume 512 exists between the top cover 514 and the bottom 510.

In this embodiment, there is also a conduit 530 that facilitates translation of the mapping catheter 13 and/or the auxiliary catheter 15 from external to the test tank 500 to internal the physical heart model 22. In some embodiments, test tank 500 comprises a translation stage (e.g. a precision single, dual or triple axis translation stage) to precisely place and/or move mapping catheter 13 and/or auxiliary catheter 15.

FIG. 5 shows other holders or bracket devices 532, 534 that can be used to secure other electrodes discussed above within the test tank 20.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

We claim:

1. A cardiac virtualization system, comprising:
a test tank defining a test volume;
a physical heart model disposed within the test tank and representing a heart surface and/or at least one heart chamber surface;
a plurality of virtualization electrodes disposed at select locations relative to the physical heart model; and
test electronics configured to drive the plurality of virtualization electrodes to generate simulated biopotentials within the test tank as if produced by a heart or at least one heart chamber at the location of the physical heart model,
wherein the virtualization electrodes are configured to simulate a surface charge density pattern and/or a dipole density pattern under the heart surface and/or under the at least one heart chamber surface.

2. The system of claim 1, wherein the virtualization electrodes are configured to simulate a surface charge density pattern and/or a dipole density pattern on the heart surface and/or on the at least one heart chamber surface.

3. The system of claim 1, wherein the test tank forms an electrically inert fixture that does not conduct or reflect electrical energy.

4. The system of claim 1, wherein the test tank is made from a material taken from a group consisting of one or more of glass, plastic, resin, Plexiglas, and fiberglass.

5. The system of claim 1, wherein the test volume is smaller than a volume of the test tank.

6. The system of claim 1, wherein the test volume is filled with a test fluid that is electrically transmissive.

7. The system of claim 6, wherein the test fluid is saline.

8. The system of claim 1, wherein the test tank comprises a plurality of electrode holders configured to secure the virtualization electrodes in place.

9. The system of claim 1, further comprising:
a support structure configured to hold the physical heart model at a selected position and 3D orientation within the test volume.

10. The system of claim 9, wherein the support structure includes a frame within which the physical heart model is maintained and a base plate that supports the frame.

11. The system of claim 1, wherein the physical heart model is electrically inert.

12. The system of claim 1, wherein the physical heart model includes a plurality of perforations that enable the test fluid to pass through.

13. The system of claim 1, wherein the physical heart model is generated by a 3D printer from a heart data file comprising information representing the physical size and shape of a heart or at least one heart chamber.

14. The system of claim 13, wherein the heart data file is processed by the system to drive the 3D printer to generate the physical heart model.

15. The system of claim 1, wherein the test electronics drive the plurality of electrodes to generate the simulated biopotentials based on an electrophysiological (EP) model representing the cardiac activity of the heart or at least one heart chamber.

16. A cardiac virtualization system, comprising:
a test tank defining a test volume;
a physical heart model disposed within the test tank and representing a heart surface and/or at least one heart chamber surface;
a plurality of virtualization electrodes disposed at select locations relative to the physical heart model; and
test electronics configured to drive the plurality of virtualization electrodes to generate simulated biopotentials within the test tank as if produced by a heart or at least one heart chamber at the location of the physical heart model,
wherein the heart or at least one heart chamber is a real heart or at least one real heart chamber.

17. The system of claim 1, wherein the heart or at least one heart chamber is a simulated heart or at least one simulated heart chamber.

18. The system of claim 17, wherein the simulated heart or at least one simulated heart chamber includes only simulated heart data.

19. The system of claim 1, wherein the heart or at least one heart chamber includes real and simulated heart data.

20. The system of claim 1, further comprising an actuator configured to move at least a portion of the physical heart model, wherein the movement simulates the natural movement of heart tissue.

21. The system of claim 20, wherein the actuator comprises a component selected from the group consisting of: a solenoid, a linear actuator, a piston; a shaped memory component; and combinations thereof.

* * * * *